United States Patent [19]

Spicer et al.

[11] Patent Number: 5,211,952

[45] Date of Patent: May 18, 1993

[54] CONTRACEPTIVE METHODS AND FORMULATIONS FOR USE THEREIN

[75] Inventors: Darcy V. Spicer, Pasadena; Malcolm C. Pike, Long Beach, both of Calif.

[73] Assignee: University of Southern California, Los Angeles, Calif.

[21] Appl. No.: 684,612

[22] Filed: Apr. 12, 1991

[51] Int. Cl.$^5$ .................. A61F 2/02; A61F 6/06; A61K 37/38; A61K 9/50; A61K 9/14; C07K 15/06; C07K 17/02; C07K 17/14

[52] U.S. Cl. .................. 424/426; 424/423; 424/424; 424/430; 424/432; 424/433; 424/484; 424/485; 424/486; 424/487; 424/488; 424/489; 424/DIG. 14; 424/449; 514/2; 514/12; 514/21; 514/800; 514/841; 514/842; 514/843; 530/850; 530/853; 128/830; 128/832; 128/833

[58] Field of Search .......... 424/422, 423, 424, 426, 424/430, 432, 433, 484, 485, 486, 487, 488, 489, 490, 496, 497, 498, DIG. 14; 514/2, 12, 21, 800, 841, 842, 843; 530/313, 850, 853; 128/830, 832, 833

[56] References Cited

U.S. PATENT DOCUMENTS

| | | | |
|---|---|---|---|
| 4,264,575 | 4/1991 | Zimmerman et al. | 424/432 |
| 4,762,717 | 8/1988 | Crowley, Jr. | 424/425 |

OTHER PUBLICATIONS

Bergkvist, et al. *N.E. Journal of Medicine* 321:293-97 (1989).
Conn et al. *N.E. Journal of Medicine* 324: 93-103 (1991).
Donnez et al. *Fertility and Sterility* 51: 947-50 (1989).
Cowsar et al. *Long Acting Contraceptive Delivery Systems* pp. 145-162 (eds. Zatuchni et al. 1984).
Ferguson et al. *Journal of Controlled Release* 8: 45-54 (1988).
Friedman *Fertility and Sterility* 51: 526-28 (1989).
Garza-Flores et al. *Contraception* 30: 371-79 (1984).
Gilley et al. *Southern Research Inst.* 73-73.
Hahn et al. *Long Acting Contraceptive Delivery Systems*, pp. 97-112 (eds. Zatuchni et al. 1984).
Hsieh et al. *Rutgers Univ.* pp. 134-135.
Hsieh et al. *Drug Development and Industrial Pharmacy* 11(6&7): 1391-1410 (1985).
Kaufmann et al. *Journal of Clinical Oncology* 7: 1113-1119 (1989).
Lewis et al. *Long Acting Contraceptive Delivery Systems* pp. 76-95 (eds. Zatuchni et al. 1984).
Lobo et al. *Amer. Journal of Obstetrics & Gyn.* 138: 714-719 (1980).
Nezhat et al. *Amer. Journal of Obstetrics & Gyn.* 138: 1151-1156 (1980).
Nuwayser et al. *Long Acting Contraceptive Delivery Systems* pp. 65-75 (eds. Zatuchni et al. 1984).
Pitt et al. *Long Acting Contraceptive Delivery Systems* pp. 49-63 (eds. Zatuchni et al. 1984).
Sandow et al. *LHRH Analogues in Gyn.* pp. 16-31.
Zorn et al. *Fertility & Sterility* 53:401–406 (1990).

*Primary Examiner*—Thurman K. Page
*Assistant Examiner*—Carlos Azpuru
*Attorney, Agent, or Firm*—Robbins, Dalgarn, Berliner & Carson

[57] ABSTRACT

Contraceptive devices which are effective for extended periods of time are described, in the form of means for releasing an effective amount of a gonadotropin hormone releasing hormone composition and means for releasing an effective amount of an estrogenic hormone over a first period of time, and means for releasing an effective amount of a progestogen for a second period of time, the second period of time being substantially shorter than and running simultaneously with a portion of the first period of time. The gonadotropin hormone releasing hormone composition is selected from gonadotropin hormone releasing hormone, gonadotropin hormone releasing hormone analogues, gonadotropin hormone releasing hormone agonists, gonadotropin hormone releasing hormone antagonists and mixtures thereof. Contraceptive methods employing the devices are also described.

16 Claims, No Drawings

CONTRACEPTIVE METHODS AND FORMULATIONS FOR USE THEREIN

BACKGROUND OF THE INVENTION

This invention relates to methods for inhibiting conception in mammals, especially human females, and to formulations for use in such methods. More particularly, the present invention is directed to contraceptive methods and preparations for use therein effective for extended periods of time.

Gonadotropin releasing hormone (GnRH), also known as luteinizing hormone releasing hormone (LHRH), produced by the hypothalamus controls the secretion of follicle stimulating hormone (FSH) and luteinizing hormone (LH) by the pituitary and thence gonadal steroid hormone production. Potent synthetic agonists of GnRH administered to premenopausal women have been shown to produce a transient rise in FSH/LH release followed by a sustained suppression. Immediately after GnRH agonists became available in the late 1970s, a number of approaches to the use of a GnRH agonist as a contraceptive were explored. Among these approaches, inhibition of ovulation by the chronic administration of GnRH agonists appeared to offer the greatest potential. It was hoped that GnRH agonists would form the basis of an improved method of contraception by offering greater convenience, increased effectiveness or fewer side effects than is the case with combination-type oral contraceptives (COCs).

Inhibition of ovulation by GnRH agonists has been found, as expected, to be dose-related. When administered in a dose just high enough to ensure anovulation, the ovaries may continue to produce estrogen. This is an unstable situation, with different women having widely varying serum estrogen levels. There has also been concern that endometrial hyperplasia would occur in some women, while in others there would be periods of hypoestrogenemia with unacceptable vasomotor symptoms and probably loss of bone mineral content.

"High-dose" GnRH agonists have been observed to uniformly reduce serum estradiol and serum progesterone to oophorectomized levels. The development of "high dose" depot formulations of GnRH agonists permits sustained inhibition of ovulation and suppression of ovarian steroid production, as well as improved ease of drug administration. The treatment is reversible; in a study of 50 patients, recovery of menstrual function occurred on average at 87 days (range 44–126 days) following 6–8 months treatment with the GnRH agonist tryptorelin [Zorn, J.-R. et al., *Fertil.Steril.* 53:401–06 (1990)]. Other depot formulations of GnRH agonists produce similar sex-steroid suppression including decapeptyl [George, M. et al., *Int. J. Fertil.* 34:19–24 (1989)], goserelin [Kaufman, M. et al., *J. Clin. Oncol.* 7:1113–19 (1989)]and buserelin [Donnez, J. et al., *Fertil. Steril.* 51:947–50 (1989)].

In spite of their clear effectiveness as contraceptive agents, side effects attendant to the use of "high-dose" GnRH agonists for prevention of pregnancy has prevented their general adoption. Common side effects reported to occur in depot GnRH agonists in premenopausal patients include: hot flashes, vaginal dryness, irregular vaginal bleeding and fatigue. Additional side effects that have been reported in some patients receiving GnRH agonists include: sweating, headache, depression, lability in mood, nausea and/or vomiting, nervousness, insomnia, pollakisuria, weight gain, sleepiness, dizziness, decreased libido and mild breast tenderness or swelling.

A recent review article reflects current thinking about GnRH and its analogues (Conn, P. M. and Crowley, Jr., W. F., "Gonadotropin-Releasing Hormone and Its Analogues," *N. Enol. J. Med.* 324:93–103 (1991)). The authors note at pages 96–97 that "whether to supplement GnRH-agonist analogues with sex steroids is a complex decision"; they propose estrogen replacement followed by the administration of a progestational agent "at physiologic doses and in a physiologic (i.e., sequential) pattern."

U.S. Pat. No. 4,762,717 to Crowley, Jr., the entire disclosure of which is hereby incorporated by reference, is based on the above-noted assumption that administration of a progestational agent should be effected in a sequential pattern so as to mimic the phases of the menstrual cycle. The patent describes contraceptive methods for female animals using luteinizing hormone releasing hormone (LHRH) compositions in combination with sex steroids. The patent calls for administering LHRH (or analogs, agonists or antagonists thereof) in a first delivery system combined with continuous administration of an effective amount of estrogenic steroids during the "follicular phase" of the menstrual cycle beginning at the onset of "normal menses". A second delivery system is administered during the "luteal phase" of the menstrual cycle until the onset of "normal menses". The second delivery system comprises the LHRH/estrogenic steroid combination and additionally provides an effective dosage of a progestational steroid.

This administration sequence is designed to mimic the physiological secretion o steroids in the menstrual cycle. As a consequence, each delivery system is effective for a period of only about two weeks (corresponding to the typical length of each of the follicular and luteal phases, according to the designation of Crowley). The progestational steroid according to Crowley is administered for fully half the time of the treatment program (i.e., throughout the time interval when the second delivery system is in use).

The approach of Crowley is clearly unacceptable when considered in light of current knowledge about the long-term effects of administering the components thereof for the periods of time specified. The proposed level of estrogen administration (i.e., to achieve an estradiol concentration of about 50 to about 140 pg/ml for a human female) in the two delivery system approach of Crowley is unnecessarily high and the proposed duration of progestogen use unnecessarily lengthy. Epidemiologic case-control studies of postmenopausal breast cancer risk and estrogen replacement therapy (ERT) using population controls suggest that increased exposure to exogenous estrogen leads to an increased risk of breast cancer in a dose-dependent fashion. Moreover, administration of progestational steroid for about two weeks of every approximately 28-day treatment cycle was associated with unacceptable risks to the patient in a recent epidemiological study [Bergkvist, L. et al., *N. Engl. J. Med.* 321:293–97 (1989)]; the study suggests that the addition of progestogen during the latter half of the 28-day ERT cycle may double the risk associated with use of estrogen alone.

Pike, M. C. et al., *Br. J. Cancer* 60:142–48 (1989), the entire disclosure of which is also hereby incorporated by reference, have proposed a contraceptive regimen in which "high-dose" LHRH agonist treatment is coupled with estrogen replacement therapy (ERT), specifically 0.625 mg of conjugated equine estrogens for 21 days in each 28-day treatment cycle. The administration of a progestational steroid is proposed to be limited to a 10–16 day interval every three or four cycles. It is now clear that the 7-day period in each treatment cycle when ERT is not provided would be associated in many patients with symptoms of estrogen withdrawal, such as hot flushes. Moreover, a negative calcium balance could develop during the period of hypoestrogenemia with the possibility of resultant osteoporosis. Finally, blood cholesterol levels would likely be adversely affected during that time. Therefore, it is unlikely that the specific regimen proposed by Pike et al. would be found acceptable.

It is an object of the present invention to provide a contraceptive regimen which would obviate the problems attendant to the use of existing methods of birth control, while at the same time reducing the risk of adverse consequences associated with the heretofore known methods.

BRIEF DESCRIPTION OF THE INVENTION

In accordance with the present invention, there is provided a contraceptive protocol which consists of continuous administration of a GnRH composition at a dose sufficient to completely suppress ovarian steroid production, in combination with a precisely formulated regimen of add-back steroids. In particular, in accordance with the present invention there is provided a contraceptive delivery system and method for preventing pregnancy in a mammal (in particular, a human female) which comprises administering over an extended period of time (on the order of about 2 to about 6 months) an amount of a GnRH composition effective to suppress LH and FSH (with resultant inhibition of ovulation and ovarian sex-steroid production); an amount of an estrogenic steroid effective to counteract the possibility of side effects which may develop during prolonged therapy with GnRH, including but not limited to: symptoms of the menopause, vasomotor instability, loss of bone mineral content, rise in serum total or low-density cholesterol or its fractions, and urogenital atrophy; together with a short-term administration (on the order of about 5 to 20 days, preferably 10 to 15 days) of an amount of progestational steroid effective to counteract the possibility of endometrial hyperstimulation, hyperplasia or carcinoma which may develop during prolonged therapy with estrogenic steroids.

Use of delivery systems for long-term release of GnRH agonists, requiring infrequent administration, makes the inventive regimen both practical and potentially more effective than COCs. As ovulation would be prevented by the GnRH agonist, the amount of add-back steroids administered is substantially reduced from that in conventional COCs. Moreover, in accordance with the present invention the levels of estrogen replacement would be significantly lower than those proposed as suitable in human female patients by Crowley. Further, the administration of progestational steroid would not be effected every menstrual cycle, as proposed by Crowley; rather, progestational steroid would be provided only once for a relatively short time interval over each extended period of time, and only for a second, relatively short time interval.

The contraceptive regimen of the present invention exhibits greater contraceptive effectiveness than currently available contraceptive protocols, such as the use of COCs. In addition, the use of a long-term administration depot provides significantly greater convenience of administration. The reduction in the amount of sex steroids administered also has the effect of reducing the projected rate of incidence of breast cancer, as well as reducing the incidence of various benign gynecological disorders. The invention further reduces the risk of ovarian cancer, as is known to occur with COC use.

DETAILED DESCRIPTION OF THE INVENTION

Pursuant to the present invention, the contraceptive regimen comprises a slow-release (or depot) formulation which is effective for an extended period of time. This extended period of time is substantially longer than is the case with either delivery system of Crowley, each of which is designed to be replaced after only a two-week period. Typically, the depot formulation of the invention is effective over an extended period of time of at least about two months. Depending on the composition and mode of administration, the inventive formulation may be effective for as long as about six months or more. It is presently preferred that the formulation be effective over about a three or four month period.

A number of compounds have been developed to inhibit effective release or action of gonadotropin releasing hormone (GnRH), including both agonists and antagonists of GnRH. While the following detailed disclosure describes in particular the use of GnRH agonists, other GnRH analogues (such as GnRH antagonists) and GnRH itself may also be employed in a manner known per se for essentially complete prevention of pregnancy in formulations in accordance with the invention, and are hereinafter referred to as "GnRH compositions". The GnRH compositions provide continuous suppression of pituitary gonadotropin secretion, thereby inhibiting ovulation.

A GnRH agonist formulation, leuprolide acetate depot (LAD), is commercially available in the United States and lasts about 4 weeks. A 16-week formulation of buserelin has been tested [Donnez, J. et al., *Fertil. Steril.* 51:947–950 (1989)]. Longer acting formulations of leuprolide acetate or other gonadotropin compositions are also contemplated as within the scope of the invention. Other suitable GnRH compositions which may be administered in a suitable time-release formulation are described in the aforementioned U.S. Pat. No. 4,762,717 and the patents cited therein. These include decapeptyl, buserelin, nafarelin, deslorelin, histrelin, gonadorelin and [(Imbzl)-D-His$^6$-Pro$^9$-Net]GnRH.

The dose of GnRH composition must be sufficient to completely suppress ovarian estrogen production, so that estrogen effects are predictably related to the administered estrogen. The amount of GnRH composition effective to achieve the desired suppression of ovarian estrogen production may readily be determined with respect to any given GnRH composition and for any given mammal. In the combined administration of an effective dose of GnRH composition, the dose range depends upon the particular GnRH composition used, but is in an amount effective to suppress LH and FSH. The effective dose ranges, as well as being compound specific, may also depend upon patient characteristics, such as age and weight. Further, the effective amount of GnRH composition also depends upon route of administration. Thus, administration by subcutaneous or intramuscular routes typically requires less GnRH composition than administration by transdermal or vaginal routes. An effective dose range of GnRH composition is thus determined by routine testing by one of skill in the art without undue experimentation. The GnRH composition may comprise a single active agent or a combination of two or more such agents. In general, it is expedient to administer the active GnRH composition in an amount between about 0.0001 and 10 mg/kg of body weight per day. It is understood in the art that this range may vary depending upon whether a GnRH antagonistic analogue or a GnRH agonistic analogue, or combination of the two, is administered.

GnRH compositions are in general absorbed very well across a wide variety of surfaces. Thus, subcutaneous, intramuscular, vaginal and transdermal routes of administration have all proven to be effective, and would be suitable for use in accordance with the present invention. In an embodiment of this invention, administration of the delivery system is made via the intramuscular route. Thus, the GnRH composition is administered via an intramuscular delivery system using an excipient which effects a slow degradation of the delivery system.

As previously noted, the use of a GnRH composition alone as a suitable method for contraception had effectively been abandoned in view of the side effects attendant thereto. Most, if not all, of the side effects of GnRH composition use reflect the hypoestrogenic state induced and can thus be prevented in accordance with the present invention by add-back estrogen therapy. Accordingly, a second component of a contraceptive regimen in accordance with the present invention is an effective amount of an estrogenic steroid to prevent symptoms and signs of the menopause, including loss of bone mineral content and adverse alterations in serum cholesterol.

As the add-back estrogen, a single-component natural or synthetic estrogen composition or a combination of such compositions can be used to maintain a constant systemic level. A substantial body of information exists concerning the effects of hormone replacement therapy after a natural or surgical menopause. Although more is known about the effects of conjugated equine estrogens (CEE) as estrogen replacement therapy (ERT) than any other agent, it is presently preferred that a single-component or two-component composition be employed.

As used herein, estrogenic steroids refer to both the natural and the synthetic materials. These materials are well known in the art. Natural and synthetic estrogenic compositions which can be used according to the invention described herein include natural estrogenic hormones and congeners, including but not limited to estradiol, estradiol benzoate, estradiol cypionate, estradiol valerate, estrone, diethylstilbestrol, piperazine estrone sulfate, ethinyl estradiol, mestranol, polyestradiol phosphate, estriol, estriol hemisuccinate, quinestrol, estropipate, pinestrol and estrone potassium sulfate. Equine estrogens, such as equilelinin, equilelinin sulfate and estetrol, may also be employed.

Typical dose ranges for estrogenic steroids depend not only upon the choice of steroid, but also upon the characteristics of the patient. For an adult human female patient administered estradiol, typical dose ranges are such that the serum level of estradiol is maintained at a level of about 25 to about 140 pg/ml. Most preferably, the serum level of estradiol is about 30 to about 50 pg/ml, which is significantly lower than the preferred serum level of 80 to 120 pg/ml called for by Crowley.

In accordance with the present invention, the effective dosage of an estrogenic steroid is delivered in the same delivery system as the GnRH composition, although the excipient composition and/or formulation may differ. The delivery system thus allows complete suppression of gonadotropins, removal of reproductive function of the ovaries, and complete suppression of ovarian steroidogenesis for the extended period of time for which the system is designed to be effective; at the same time, there is a replacement of sufficient levels of estrogen to minimize or eliminate the long-term side effects of GnRH composition administration.

The third component of the inventive regimen is a progestogen. Unlike the GnRH composition and estrogen replacement, which are administered at a continuous level for an extended period of time equal to the duration of the treatment cycle, the progestogen component is present in an amount sufficient to provide suitable systemic levels for only a second, more limited period of time. Typically, the progestogen is administered for a period of time on the order of 5 to 20 days, and preferably 10 to 15 days. The progestogen is provided in an amount effective to minimize or eliminate the occurrence of endometrial hyperplasia by substantially reducing the possibility of endometrial hyperstimulation which may occur during prolonged treatment with estrogenic steroids without a progestogen. In accordance with the present invention, the progestogen is delivered in the same delivery system as the GnRH composition and the estrogenic composition, although the excipient composition and/or formulation may differ to permit release of the progestogen over the second shorter time period.

Unlike the method proposed by Crowley, administration of progestogen in preferred embodiments of the present invention is generally not repeated every 28 days (corresponding to the length of the normal menstrual cycle). Rather, the progestogen component is provided in these preferred embodiments only for the initial phase of each extended treatment regimen. Suitably, a treatment cycle in accordance with the present invention comprises about two to about six months, and most preferably three or four months.

Suitable progestational agents (progestogens) for use in accordance with the present invention include but are not limited to dydrogesterone, ethynodiol diacetate, hydroxyprogesterone caproate, medroxyprogesterone acetate, norethindrone, norethindrone acetate, norethynodrel, norgestrel, progesterone, and megestrol acetate. Typical dose ranges for progestogens depend upon the choice of steroid and the individual patient. For an adult human female administered progesterone, typical doses are administered to provide serum levels of progesterone of from about 5 to about 20 ng/ml, and preferably about 5 to about 10 ng/ml, during the time interval of progestogen treatment (about 5 to about 20 contiguous days, and preferably about 10 to about 15 contiguous days). The serum level of progesterone is generally less than 5 ng/ml after the time interval of progestogen treatment; preferably, the serum level of progesterone is less than 1 ng/ml after the time interval of progestogen treatment.

In accordance with the present invention, the delivery vehicle of the invention provides for administration of GnRH composition, estrogen and progestogen by a subcutaneous, intramuscular, vaginal or transdermal route. The carrier vehicle for each component is selected from a wide variety of materials which are already known per se or may hereafter be developed which provide for controlled release of the compositions in the particular physiological environment. In particular, the carrier vehicle of the delivery system is selected such that near zero-order release of the components of the regimen is achieved. In the context of the present invention, the carrier vehicle should therefore also be construed to embrace particular formulations of the compositions which are themselves suitable for providing near zero-order release. A targeted steady-state release can be obtained by suitable adjustment of the design or composition of the delivery system.

One suitable formulation to achieve the desired near zero-order release of the components comprises injectable microcapsules or microspheres prepared from a biodegradable polymer, such as poly(dl-lactide), poly(dl-lactide-co-glycolide), polycaprolactone, polyglycolide, polylactic acid-co-glycolide, poly(hydroxybutyric acid), a polyortho-ester or a polyacetal. Injectable systems comprising microcapsules or microspheres of a diameter on the order of about 50 to about 500 μm offer advantages over other delivery systems. For example, they generally use less hormone and may be administered by paramedical personnel. Moreover, such systems are inherently flexible in the design of the duration and rate of separate drug release by selection of microcapsule size, drug loading and dosage administered. In addition, such microcapsules can be successfully sterilized with gamma irradiation.

Microcapsules are systems comprising a polymeric wall that encloses a liquid or solid core. The capsule wall usually does not react with the core material; however, it is designed to provide sufficient strength to enable normal handling without rupture while being sufficiently thin to allow a high core to wall volume ratio. The capsule contents remain within the wall until released by diffusion or other means that dissolve, melt, break, rupture or remove the capsule material. Preferably, the capsule wall can be made to degrade and decompose in suitable environments while diffusing the core material through the capsule wall to allow for its slow, prolonged delivery.

The mechanism of release in biodegradable microcapsules is a combination of drug diffusion and polymer biodegradation. Therefore, the rate and duration of release are determined by microcapsule size, drug content and quality, and polymer parameters, such as crystallinity, molecular weight and composition. In particular, adjustment in the amount of drug released is generally achieved by modification of capsule wall thickness, capsule diameter, or both. Detailed information concerning the design and use of microspheres and microcapsules is provided by, e.g., Lewis, D. H., "Controlled Release of Bioactive Agents from Lactide/Glycolide Polymers," in Jason & Langer (eds.), *Biodegradable polymers as drug delivery systems*, pp. 1–41 (1990), the entire disclosure of which is hereby incorporated by reference.

Several methods are currently available for preparing microcapsules. As discussed in Nuwayser, E. S. et al., "Microencapsulation of Contraceptive Steroids," in Zatuchni, G. L. et al. (eds.), *Long-acting contraceptive delivery systems*, pp. 64–76 (1984), the entire disclosure of which is hereby incorporated by reference, most of these methods can be classified under three major categories: coacervation, coagulation and air-suspension coating.

An exemplary material for use in the formulation of suitable microcapsules or matrix formulations is poly(dl-lactide-co-glycolide) as described in Lewis, D. H. and Tice, T. R., "Polymeric Considerations in the Design of Microencapsulation of Contraceptive Steroids," in Zatuchni, G. L. et al. (eds.), *Long-acting contraceptive delivery systems*, pp. 77–95 (1984), the entire disclosure of which is hereby incorporated by reference. The solvent evaporation process described therein is suitable for preparing microcapsules in a size range acceptable for administration by conventional syringe and needle; moreover, the yield or fraction of microcapsules within a desired size range can be selected and achieved with appropriate process adjustments. This enables the preparation of diffusional controlled-release formulations in which the duration of drug release is directly related to total surface area or microcapsule particle size. Another exemplary material is poly($\epsilon$-caprolactone) as described in Pitt, C. G. and Schindler, A., "Capronor—A Biodegradable Delivery System for Levonorgestrel," in Zatuchni, G. L. et al. (eds.), *Long-acting contraceptive delivery systems*, pp. 48–63 (1984), the entire disclosure of which is hereby incorporated by reference. Other biodegradable polymeric materials suitable for preparation of microcapsules for controlled (i.e., near zero-order) release would be readily determined through routine experimentation by those skilled in the art.

An alternative delivery system suitable for use in accordance with the present invention comprises fibers or filaments comprising the active agents and biodegradable or nonbiodegradable polymers. Precision delivery systems can be mass-produced by this method; moreover, geometrically configured controlled-release devices can be produced by, e.g., wrapping drug-releasing fibers around conventional intravaginal rings or other intravaginal devices. Typically, fibrous delivery systems rely on membrane-moderated diffusion mechanisms to control the rate and duration of drug release. Monolithic drug-releasing fibers may be prepared by conventional spinning processes; when reservoir-type fibrous systems are desired, either a fast-releasing monolithic fiber is prepared and then coated with a rate-controlling sheath, or a coaxial spinning process is employed, in which the drug is extruded as the core of the fiber at the same time as the rate-controlling polymer sheath. Suitable fibers for providing zero-order release of the active agents and methods for the preparation thereof are described in Cowsar, D. E. and Dunn, R. L., "Biodegradable and Nonbiodegradable Fibrous Delivery Systems," in Zatuchni, G. L. et al. (eds.), *Long-acting contraceptive delivery systems*, pp. 145–163 (1984), the entire disclosure of which is hereby incorporated by reference.

Other suitable materials for preparation of such intravaginal devices include silicon-based materials, such as polydimethylsiloxanes, which have been employed to prepare capsule-type, matrix-type and microsealed drug delivery systems. For example, a suitable device may be prepared by coating a nonmedicated silicone rubber core with a thin layer of silicone rubber (such as MDX-4-4210 Clean Grade Elastomer, available from Dow Corning) which contains micronized crystalline forms of the active agents. An implant of this type (for administration of estradiol-17B) is described in Ferguson, T. H. et al., "Compudose: An Implant System for Growth Promotion and Feed Efficiency in Cattle," *J. Controlled*

*Release* 8, pp. 45–54 (1988), the entire disclosure of which is hereby incorporated by reference. Improved devices may be prepared by incorporating water-soluble carriers, such as sodium alginate, or by using additives, such as co-solvents or salts, which enhance the release rate of active agents from the polymer matrix.

In general, contraceptive vaginal rings may be designed as homogeneous mixtures of steroid and silastic; as a core vaginal ring surrounded by silastic; as a shell ring with a core of silastic, surrounded by a layer of steroid and silastic covered by a tube of silastic; as a band ring of inert silastic with a drug-containing band on the ring; or as a combination of the various designs to permit the specific release characteristics desired. In this regard, useful systems are described in the following: Jackanicz, T. M., "Vaginal Ring Steroid-Releasing Systems," pp. 201–212; Diczfalusy, E. and Landgren, B.-M., "Some Pharmacokinetic and Pharmacodynamic Properties of Vaginal Delivery Systems That Release Small Amounts of Progestogens at a Near Zero-Order Rate," pp. 213–227; and Roy, S. and Mishell, Jr., D. R., "Vaginal Ring Clinical Studies: Update," pp. 581–594, all in Zatuchni, G. L. et al. (eds.), *Long-acting contraceptive delivery systems* (1984), the entire disclosures of which are hereby incorporated by reference.

For transdermal delivery of the active agents, suitable pads or bandages are also well known in the art. Typically, these pads comprise a backing member defining one exterior surface, a surface of pressure-sensitive adhesive defining a second exterior surface, and disposed therebetween a reservoir containing the active agents confined therein. Suitable transdermal delivery systems are disclosed in U.S. Pat. Nos. 3,731,683 and 3,797,494 to Zaffaroni and U.S. Pat. No. 4,336,243 to Sanvordeker et al., the entire disclosures of which are hereby incorporated by reference.

Other suitable formulations would be readily apparent to those of skill in the art. For example, with certain active agents, administration may be effected subcutaneously or intramuscularly with slowly-dissolving pellets of crystalline or microcrystalline materials, or directly as a crystalline or microcrystalline aqueous suspension. The important features are maintenance of near zero-order release of the drugs over the desired treatment periods, followed by a relatively rapid decrease in serum concentrations to low levels once the relevant portion of the treatment regimen has been completed.

The inventive regimen is designed to reduce the degree of adverse effects associated with the use of GnRH compositions, estrogen and progestogen in accordance with the heretofore known protocols, such as those of Crowley and Pike et al. For example, GnRH compositions have been recognized as having an adverse impact on bone metabolism. Bone mineral density (BMD) is known to fall after a natural or surgical menopause; the fall is most evident in regions of trabecular bone. A net loss of BMD has been seen in the majority of studies after 6 months of GnRH agonist treatment, well in excess of even the greatest rates of fall of approximately 1%/yr that have been reported in premenopausal women. In accordance with the present invention, ERT alone or combined with a progestogen is administered to reduce BMD loss in postmenopausal women. The reduction in BMD loss is mirrored in a much reduced fracture risk in ERT treated postmenopausal women. Similarly, the ability of ERT to control hot flashes and other menopausal symptoms is also well documented.

By combining GnRH composition therapy with appropriate levels of estrogen and progestogen replacement therapy the effects of the hypoestrogenic state induced by the GnRH composition are prevented.

An increased risk of cardiovascular disease has been a further concern with the long-term use of a GnRH composition, as such an increase has been associated with oophorectomy at a young age. According to the present invention, add-back estrogen is employed to reduce the risk of cardiovascular disease. As is the case when ERT is given to postmenopausal women, a major reason for this reduction in risk is likely to be the beneficial effects of estrogen on serum cholesterol. GnRH agonists may have effects on cholesterol which are not mediated by their effects on serum estradiol. The inventive regimen is predicted to result in a beneficial rise in high density lipoprotein cholesterol or HDLC (increase from GnRH agonist and from add-back estrogen) and no change in low density lipoprotein cholesterol or LDLC (increase from GnRH agonist balanced by comparable decrease from add-back estrogen), a clearly beneficial overall effect. The addition of progestogen may slightly decrease HDLC, but the overall predicted effect of the proposed regimen remains highly beneficial.

While estrogen thus has significant positive effects in conjunction with the use of a GnRH composition, it is nonetheless important to recognize the potential risks inherent in such treatment. For example, a substantial body of evidence has shown that ovarian hormones are critical factors in the etiology of breast cancer. Inducing a reversible "medical oophorectomy" through the use of a GnRH composition given at a dose sufficient to suppress ovarian function to postmenopausal levels in accordance with the present invention similarly achieves a major reduction in a woman's lifetime breast cancer risk relative to the use of COCs. Add-back therapy with low-dose estrogen and progestogen is, however, required to prevent harmful hypoestrogenic effects and to protect the endometrium. Thus, the present invention strives for an appropriate balance in the combined effect of a GnRH composition and the add-back hormone regimen so as to minimize subsequent breast cancer risk.

If there were no increased breast cancer risk from ERT and progestogen use in the postmenopausal period, then the prototype GnRH composition plus add-back estrogen plus progestogen regimen should substantially reduce breast cancer risk as it should simply be equivalent to temporary bilateral oophorectomy. A more cautious approach is to assume that the addition of add-back estrogen to the GnRH composition regimen causes some increase in breast cancer risk when compared to the use of GnRH composition alone, and that the addition of progestogen may increase the risk further.

To estimate conservatively the effect on breast cancer risk of the prototype contraceptive regimen, it is assumed that the effect of the progestogen component is to double the increased risk from the add-back estrogen which is associated with the 28-day cycle in which it is administered. An estimate of the effect of a preferred four-month prototype contraceptive (i.e., four 28-day cycles) on lifetime breast cancer risk is shown in Table 1. Table 1 shows that lifetime breast cancer risk is predicted to be reduced in accordance with the present invention by 31% if used for 5 years and by 53% if used for 10 years.

Similarly, it is well-established that early menopause will substantially reduce endometrial cancer risk. Use of a GnRH composition at a dose sufficient to suppress ovarian function to postmenopausal levels similarly is expected to achieve a substantial reduction in a woman's risk of endometrial cancer. The addition of add-back estrogen therapy to the GnRH composition may, however, increase the endometrial cancer risk when compared to use of GnRH composition alone. Epidemiological studies of postmenopausal women show that "low-dose" ERT increases risk of endometrial cancer significantly less than "high-dose" ERT. Therefore, in accordance with the present invention, low-dose add-back estrogen with addition of a progestogen only infrequently is proposed to reduce this risk. An estimate of the effect of the preferred prototype contraceptive on lifetime endometrial cancer risk is shown in Table 1. Calculations suggest that there will be modest lifetime reduction in risk of endometrial cancer with even short-term use of the proposed regimen.

Endometrial hyperplasia is a significant clinical concern with ERT use in postmenopausal women. Progestogen therapy for 5-20 days (preferably, 10-15 days) will control endometrial hyperplasia induced by add-back estrogen and achieve the desired histological changes in the endometrium. Such a regimen is not required every month; the addition of further courses of progestational agent provides a further benefit to the endometrium, and may further improve bone metabolism, but is likely to have a deleterious effect on heart disease risk and breast cancer risk as discussed above. While a small proportion of women may develop hyperplasia if progestogens are not given every 28-day cycle, few will develop symptoms. Therefore, the present invention in preferred embodiments calls for a progestogen treatment course only every few months to eliminate any hyperplasia that has developed.

Finally, the present invention is designed to reduce the risk of ovarian cancer. Protective risk factors that have been consistently found in epidemiological studies of ovarian cancer are early menopause, high parity and use of COCs. With increasing parity or increasing duration of COC use ovarian cancer risk decreases steadily. The suppression of ovulation by GnRH compositions should protect against ovarian cancer to the same extent as do COCs. The addition of ERT plus progestogen to the GnRH composition regimen should have no effect on this reduced risk.

Table 1 shows the predicted relative risks for ovarian cancer of using the prototype contraceptive for 5, 10 or 15 years at premenopausal ages. The calculations were based on using the regimen at any time during the premenopausal period. Use for 5 years is predicted to reduce the lifetime risk of ovarian cancer by as much as 41%; use for 10 years should reduce the risk by 67%.

TABLE 1

Predicted Relative Reduction in Lifetime Risk of Cancer With Prototype Four 28-Day Cycle Contraceptive

| | Duration of Regimen (years) | | |
|---|---|---|---|
| | 5 | 10 | 15 |
| Breast | 31% | 53% | 70% |
| Endometrium | 18% | 33% | 45% |
| Ovary | 41% | 67% | 84% |

An alternative preferred three-month regimen is predicted to provide the same protection for the ovary, increased protection for the endometrium and decreased protection for the breast.

The following examples will serve to illustrate the invention without in any way being limiting thereon.

EXAMPLE 1

This example describes a delivery system for intramuscular administration over a 4-month duration. The delivery system administers a GnRH composition (buserelin), a natural estrogenic steroid (estradiol) and a natural progestogenic steroid (progesterone), such that the amount of GnRH is sufficient to suppress LH and FSH secretion during the entire period of administration, with the serum level of estradiol being maintained at about 40 pg/ml. The buserelin is provided at a dose of 6.6 mg, which is sufficient to maintain serum levels on the order of 30 pg/ml throughout the treatment cycle. The estradiol is provided in a dose of 10 mg. Both the buserelin and estradiol are provided in the form of microspheres prepared from a copolymer of lactide and glycolide; as is well known in the art, this copolymer provides for an effective time-release formulation which is biodegradable. The serum level of progesterone is maintained at about 5 to 10 ng/ml for the first 10 to 15 days after administration; thereafter, the serum level drops below 5 ng/ml before reaching a baseline level of below about 1 ng/ml for the balance of the 4-month period. The progesterone is provided in a dose of 150 mg in the form of the micronized drug.

EXAMPLE 2

This example describes a vaginal ring. A shell ring of estradiol releases about 180 μg/day and thereby achieves serum levels of about 40 pg/ml for its 120 days of use. Buserelin is also released to achieve serum levels of about 30 pg/ml. In the shell ring, a band is provided containing medroxyprogesterone acetate in silastic without a shell, to release about 1 mg/day of medroxyprogesterone acetate over about 10-15 days. The vaginal ring is replaced with a fresh ring about every 120 days.

While there have been shown and described the fundamental novel features of the invention, it will be understood that various omissions, substitutions and changes in the form and details of the contraceptive devices illustrated may be made by those skilled in the art without departing from the spirit of the invention. It is the intention, therefore, to be limited only as indicated by the scope of the following claims.

What is claimed is:

1. A composition for use in a contraceptive delivery system comprising:
    a slow-release formulation of a gonadotropin hormone releasing hormone composition which maintains serum levels of said gonadotropin hormone releasing hormone composition at a level effective to inhibit ovulation over a first period of time comprising about two months to about six months;
    a slow-release formulation of an estrogenic hormone which maintains serum levels of said estrogenic hormone at a level equivalent to a serum level of estradiol of from about 25 to about 140 pg/ml over said first period of time; and
    a slow-release formulation of a progestogen which maintains serum levels of said progestogen at a level equivalent to a serum level of progesterone of from about 5 to about 20 ng/ml for a second period of time comprising about 5 to about 20 days, said second period of time running simultaneously with a portion of said first period of time.

2. A contraceptive composition according to claim 1, wherein said gonadotropin hormone releasing hormone composition is selected from the group consisting of gonadotropin hormone releasing hormone, gonadotropin hormone releasing hormone analogues, gonadotropin hormone releasing hormone agonists, gonadotropin hormone releasing hormone antagonists and mixtures thereof.

3. A contraceptive composition according to claim 2, wherein said gonadotropin hormone releasing hormone composition is a gonadotropin hormone releasing hormone agonist selected from the group consisting of leuprolide acetate, goserelin, decapeptyl, buserelin, nafarelin, deslorelin, histrelin, gonadorelin, [(Imbzl)-D-His$^6$-Pro$^9$-Net]GnRH and mixtures thereof.

4. A contraceptive composition according to claim 1, wherein said estrogenic steroid is selected from the group consisting of estradiol, estradiol benzoate, estradiol cypionate, estradiol valerate, estrone, diethylstilbestrol, piperazine estrone sulfate, ethinyl estradiol, mestranol, polyestradiol phosphate, estriol, estriol hemisuccinate, quinestrol, estropipate, pinestrol, estrone potassium sulfate, equilelinin, equilelinin sulfate, estetrol and mixtures of two or more thereof.

5. A contraceptive composition according to claim 1, wherein said progestogen is selected from the group consisting of dydrogesterone, ethynodiol diacetate, hydroxyprogesterone caproate, medroxyprogesterone acetate, norethindrone, norethindrone acetate, norethynodrel, norgestrel, progesterone, megestrol acetate and mixtures of two or more thereof.

6. A contraceptive device according to claim 1, wherein said first period of time is about three months to about four months.

7. A contraceptive device according to claim 1, wherein said second period of time is about 10 days to about 15 days.

8. A contraceptive composition according to claim 1, wherein said GnRH composition, estrogenic steroid and progestogen are administered by a subcutaneous, intramuscular, vaginal or transdermal route.

9. A method for preventing conception in a mammal, comprising:
administering an amount of a gonadotropin hormone releasing hormone composition effective to maintain serum levels of said gonadotropin hormone releasing hormone composition at a level effective to inhibit ovulation for a first period of time comprising about two months to about six months;
simultaneously administering an amount of an estrogenic hormone effective to maintain serum levels of said estogenic hormone at a level equivalent to a serum level of estradiol of from about 25 to about 140 pg/ml for said first period of time; and
administering an amount of a progestogen effective to maintain serum levels of said progestogen at a level equivalent to a serum level of progesterone of from about 5 to about 20 ng/ml for a second period of time comprising about 5 to about 20 days, said second period of time running simultaneously with a portion of said first period of time;

10. A method according to claim 1, wherein said gonadotropin hormone releasing hormone composition is selected from the group consisting of gonadotropin hormone releasing hormone, gonadotropin hormone releasing hormone analogues, gonadotropin hormone releasing hormone agonists, gonadotropin hormone releasing hormone antagonists and mixtures thereof.

11. A method according to claim 10, wherein said gonadotropin hormone releasing hormone composition is a gonadotropin hormone releasing hormone agonist selected from the group consisting of leuprolide acetate, goserelin, decapeptyl, buserelin, nafarelin, deslorelin, histrelin, gonadorelin, [(Imbzl)-D-His$^6$-Pro$^9$-Net]GnRH and mixtures thereof.

12. A method according to claim 9, wherein said estrogenic steroid is selected from the group consisting of estradiol, estradiol benzoate, estradiol cypionate, estradiol valerate, estrone, diethylstilbestrol, piperazine estrone sulfate, ethinyl estradiol, mestranol, polyestradiol phosphate, estriol, estriol hemisuccinate, quinestrol, estropipate, pinestrol, estrone potassium sulfate, equilelinin, equilelinin sulfate, estetrol and mixtures of two or more thereof.

13. A method according to claim 9, wherein said progestogen is selected from the group consisting of dydrogesterone, ethynodiol diacetate, hydroxyprogesterone caproate, medroxyprogesterone acetate, norethindrone, norethindrone acetate, norethynodrel, norgestrel, progesterone, megestrol acetate and mixtures of two or more thereof.

14. A method according to claim 1, wherein said first period of time is about three months to about four months.

15. A method according to claim 9, wherein said second period of time is about 10 days to about 15 days.

16. A method according to claim 9, wherein said GnRH composition, estrogenic steroid and progestogen are administered by a subcutaneous, intramuscular, vaginal or transdermal route.

* * * * *